(12) United States Patent
Lehmann

(10) Patent No.: US 7,470,546 B2
(45) Date of Patent: Dec. 30, 2008

(54) METHOD AND ARRANGEMENT FOR TAKING UP A FIRST MEDIUM, WHICH IS PRESENT IN A FIRST PHASE, INTO A CAPILLARY DEVICE

(75) Inventor: Volker Lehmann, Munich (DE)

(73) Assignee: Infineon Technologies AG (DE)

( * ) Notice: Subject to any disclaimer, the term of this patent is extended or adjusted under 35 U.S.C. 154(b) by 216 days.

(21) Appl. No.: 09/870,321

(22) Filed: May 30, 2001

(65) Prior Publication Data

US 2002/0127705 A1 Sep. 12, 2002

(30) Foreign Application Priority Data

May 31, 2000 (DE) ................................ 100 27 104

(51) Int. Cl.
*G01L 1/10* (2006.01)
*B01L 3/02* (2006.01)
*B01L 11/00* (2006.01)

(52) U.S. Cl. ........................ 436/180; 436/175; 422/100; 422/101

(58) Field of Classification Search ................. 422/100, 422/101; 436/180, 174–175; 73/863.32, 73/864, 864.01, 864.02, 864.11
See application file for complete search history.

(56) References Cited

U.S. PATENT DOCUMENTS

| | | | |
|---|---|---|---|
| 3,881,527 A | | 5/1975 | Shapiro |
| 3,982,438 A | | 9/1976 | Byrd |
| 4,424,132 A | * | 1/1984 | Iriguchi ........................ 210/800 |
| 4,457,184 A | * | 7/1984 | Shiono ..................... 73/864.11 |
| 4,461,328 A | * | 7/1984 | Kenney ........................ 141/67 |
| 4,511,534 A | | 4/1985 | Bennett, Jr. et al. |
| 4,532,805 A | * | 8/1985 | Flesher ..................... 73/863.32 |
| 4,596,780 A | * | 6/1986 | Castaneda ................... 436/176 |
| 4,642,220 A | * | 2/1987 | Bjorkman .................... 422/101 |
| 5,000,921 A | | 3/1991 | Hanaway et al. |
| 5,264,184 A | * | 11/1993 | Aysta et al. ................. 422/101 |
| 5,271,902 A | * | 12/1993 | Sakka et al. ................ 422/100 |
| 5,312,757 A | * | 5/1994 | Matsuyama et al. ........... 436/54 |
| 5,452,619 A | * | 9/1995 | Kawanabe et al. ....... 73/864.01 |

(Continued)

FOREIGN PATENT DOCUMENTS

DE 4214430 5/1992

(Continued)

OTHER PUBLICATIONS

Holmberg, Krister; Handbook of Applied Surface and Colloid Chemistry v1-2; Joh Wiley and Sons, Ltd.*

(Continued)

*Primary Examiner*—Brian R. Gordon
(74) *Attorney, Agent, or Firm*—Altera Law Group, LLC

(57) ABSTRACT

Method and arrangement for taking up a first medium, which is present in a first phase, into a capillary device In the capillary device, a reduced pressure is produced which is less than a critical pressure such that, if it is exerted in the capillary device, a surface tension which is produced by the first medium in the capillary device, when the first medium has been taken up fully by the capillary device, would be overcome so that a second medium which is present in a second phase, different from the first phase, would be taken up into the capillary device.

13 Claims, 3 Drawing Sheets

U.S. PATENT DOCUMENTS

| | | | |
|---|---|---|---|
| 5,464,541 A * | 11/1995 | Aysta et al. | 210/767 |
| 5,478,526 A * | 12/1995 | Sakai et al. | 422/81 |
| 5,545,531 A * | 8/1996 | Rava et al. | 435/6 |
| 5,612,227 A * | 3/1997 | Inoue et al. | 436/180 |
| 5,620,663 A * | 4/1997 | Aysta et al. | 422/104 |
| 5,639,665 A * | 6/1997 | Arai et al. | 436/50 |
| 5,811,306 A * | 9/1998 | Komatsu | 436/54 |
| 5,843,378 A * | 12/1998 | El-Hage et al. | 422/100 |
| 5,843,767 A | 12/1998 | Beattie | |
| 5,851,491 A * | 12/1998 | Moulton | 422/101 |
| 5,895,631 A * | 4/1999 | Tajima | 422/101 |
| 6,006,800 A * | 12/1999 | Nakano | 141/130 |
| 6,203,759 B1 * | 3/2001 | Pelc et al. | 422/100 |
| 6,225,130 B1 * | 5/2001 | Kitajima et al. | 436/177 |
| 6,326,212 B1 * | 12/2001 | Aoki | 436/180 |
| 6,579,724 B2 * | 6/2003 | Woodward | 436/180 |
| 6,592,825 B2 * | 7/2003 | Pelc et al. | 422/100 |
| 6,641,993 B1 * | 11/2003 | Jacobs et al. | 435/4 |
| 2001/0016358 A1 * | 8/2001 | Osawa et al. | 436/180 |
| 2002/0131903 A1 * | 9/2002 | Ingenhoven et al. | 422/100 |
| 2002/0182114 A1 * | 12/2002 | Ingenhoven et al. | 422/99 |
| 2003/0215957 A1 * | 11/2003 | Lemmo et al. | 436/180 |
| 2004/0122222 A1 * | 6/2004 | Sakurai et al. | 536/25.4 |
| 2004/0142488 A1 * | 7/2004 | Gierde et al. | 436/178 |
| 2004/0147042 A1 * | 7/2004 | Gratzl et al. | 436/180 |

FOREIGN PATENT DOCUMENTS

| | | |
|---|---|---|
| DE | 4310607 | 10/1993 |
| DE | 4209871 | 4/1997 |
| DE | 4244931 | 7/1998 |
| DE | 4244975 | 7/1999 |
| EP | 0296348 | 3/1993 |
| EP | 1161995 | 12/2001 |
| WO | WO 95/11755 | 5/1995 |

OTHER PUBLICATIONS

Taher, M. Capillary Interaction Between a Small Thin Solid Plate and a Liquid; University of Illinois at Urbana-Champaign.*
Freitas, Robert; Nanomedicine, vol. I: Basic Capabilities; 1999.*
Www.argon.iastate.solidphysics/a577cap.html; Capillarity.*
http://ising.phys.cwru.edu/surfactants/droplets.html; Droplets and Surface Tension, no date.*
Robotik und Automationskonzepte in der Kombinatorischen Chemie—Synthese- und Pipettierroboter, Nr. 1/2000, pp. 25-26, 28-29.

* cited by examiner

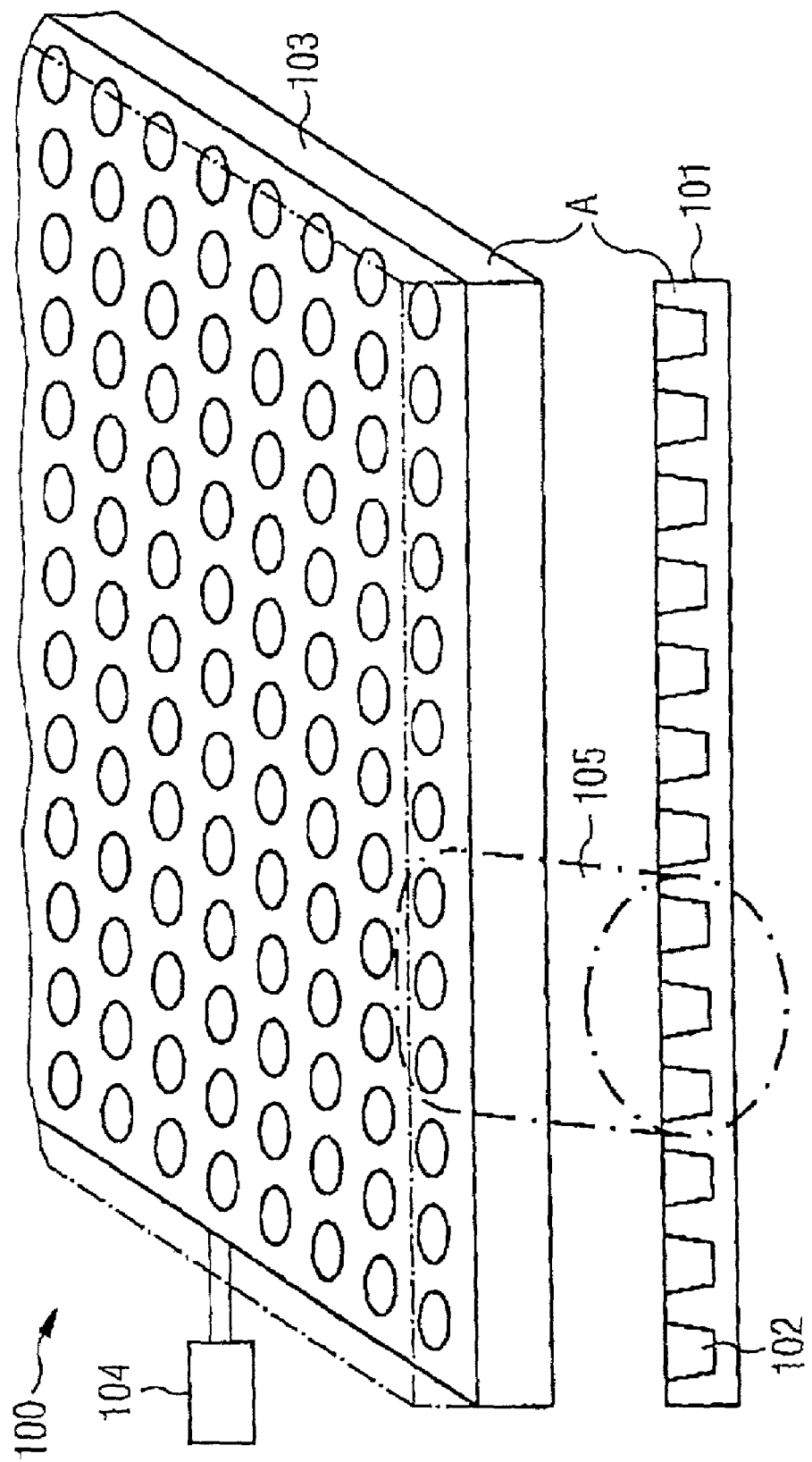

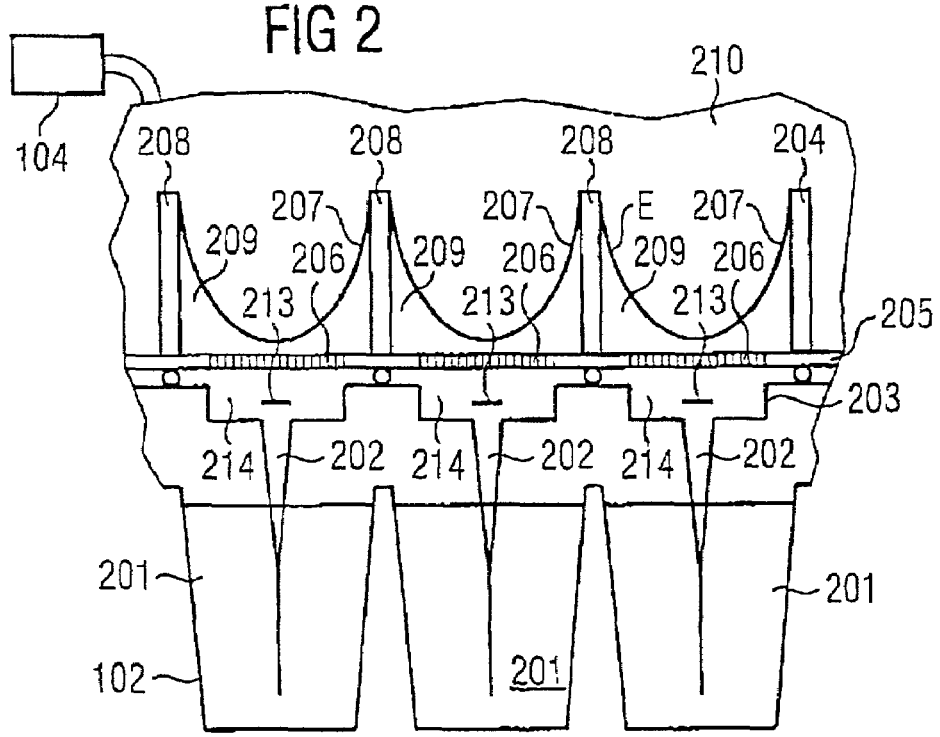
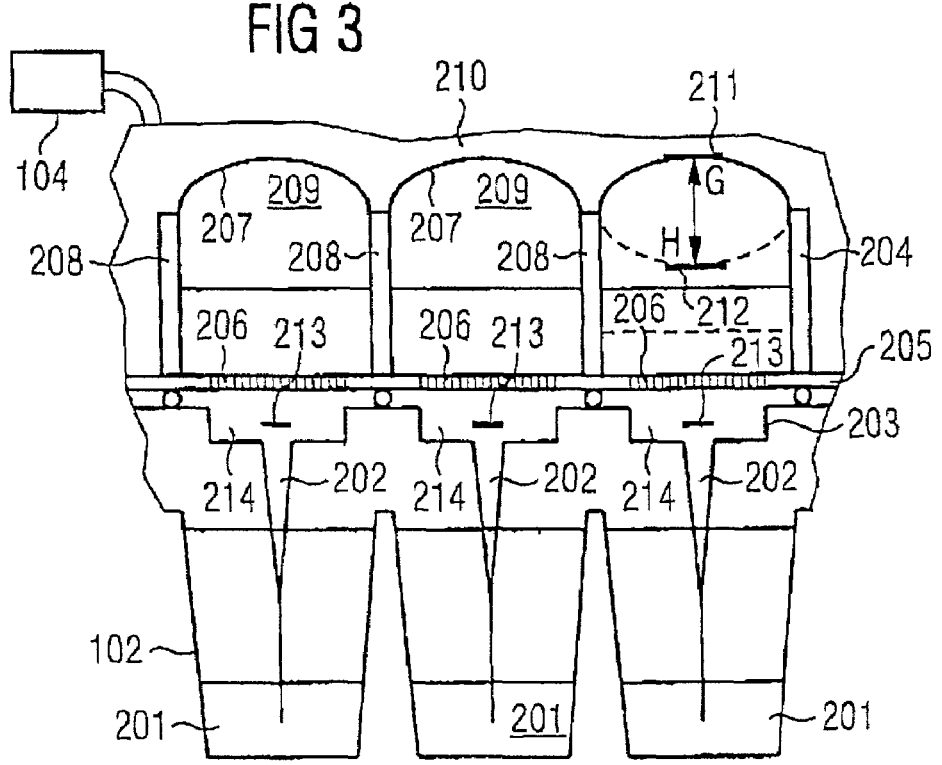

METHOD AND ARRANGEMENT FOR TAKING UP A FIRST MEDIUM, WHICH IS PRESENT IN A FIRST PHASE, INTO A CAPILLARY DEVICE

BACKGROUND OF THE INVENTION

1. Field of the Invention

Method and arrangement for taking up a first medium, which is present in a first phase, into a capillary device 2. Description of the Related Prior Art An arrangement disclosed by [1] has a microtitre plate with a plurality of wells for taking up an analyte.

Such a microtitre plate is used, for example, for a wide variety of applications in medicine and biotechnology for taking up liquids to be analysed, for example in the field of DNA analysis.

Usually, a different analyte to be analysed is introduced in each well and via a pipette, usually via a plurality of adjacently arranged elements designed as a so-called pipette comb; in a pipette comb, for example, a respective pipette is provided for each well in a row of the microtitre plate, which has wells arranged in an array.

By means of a pipette, an analyte is in each case withdrawn because of a reduced pressure created in the pipette, i.e. it is sucked up, from the corresponding well which is filled with the analyte and into which the pipette is dipped.

According to the arrangement known from [1], the pipette is in each case coupled, via tubing, to a pump which is assigned uniquely to the respective pipette, and which produces the reduced pressure, in such a way that the analyte can be sucked through the corresponding pipette by means of the pump and correspondingly can in turn be introduced into the well while being controlled by the pump.

Such a known microtitre plate has, for example, 96 wells with a size of 8 cm H 12 cm.

Such a known microtitre plate, however, may in principle have any desired number of wells, usually up to 384.

A particular disadvantage of the arrangement known from [1] is that, because of the high number of pumps, it is impractical or sometimes impossible to provide a separate pump on such a small area of 8 cm H 12 cm for each well in a row, i.e. for such a large number of pipettes.

The production of such a pipette comb, and hence of such an arrangement for taking up liquid analytes, is therefore very demanding and expensive.

It should furthermore be pointed out that, in the arrangement known from [1], a peristaltic pump is normally used in each case for sucking the analyte out of the well in question and for introducing it therein.

A considerable disadvantage of this known arrangement is furthermore that a minimum amount of an analyte to be analysed, of the order of 1 ml, is needed for the analysis.

Another disadvantage is that the large number of pumps required, with the associated tubing arrangement, is very complicated and therefore susceptible to faults.

Furthermore, [2] describes a so-called Flow-Thru Chip™, by means of which analysis of the analyte with respect to the existence of biological material in the analyte is possible.

The Flow-Thru Chip™, which is a configuration of an analysis chip, has a plurality of channels through which the analyte is fed through the analysis chip, the surface of the channels being provided respectively with probe molecules, generally with molecules which can bind, preferably covalently, the correspondingly targeted biological material whose existence in the analyte is to be detected.

If the biological material in the analyte is a DNA strand with a predefined DNA sequence to be determined, then DNA probe molecules with a sequence complementary to the DNA sequence to be determined are applied to the surface of such a liquid channel in the Flow-Thru Chip™.

If the DNA material with the targeted DNA sequence is present in the analyte, then the DNA strands bind with the corresponding DNA probe molecules of opposite, i.e. complementary sequence.

In general, such an analysis chip is often used for the analysis, i.e. for the detection of macromolecular biopolymers, examples of which include proteins or peptides as well as DNA strands with a respective predefined frequency.

Furthermore, [3] discloses the production, from glass or silicon, of a diaphragm which has a plurality of pores with a constant diameter of from 0.1 Fm to 1 Fm.

It is therefore an object of the invention to take up a first medium present in a first phase, for example as a liquid or as a gas, into a capillary device, the take-up being carried out more simply and less expensively compared with the prior art.

The object is achieved by the method and the arrangement having the features according to the independent patent claims.

In a method for taking up a first medium, which is present in a first phase, into a capillary device, a reduced pressure is produced in the capillary device. The first medium is taken up into the capillary device by the reduced pressure.

The first medium may be present as a liquid or as a gas.

For example, the first medium may be a liquid to be analysed, i.e. an analyte that will be analysed by using the capillary device and an analysis chip, which is coupled to the capillary device and with which the taken-up first medium is brought into contact.

In this case, the analysis chip is, for example, the Flow-Thru Chip™ described in [2]; biological material may be contained in the liquid channels of the analysis chip and applied to the surface of the liquid channels, the biological material being designed in such a way that biological molecules contained in the first medium can be bound by probe molecules.

For instance, DNA probe molecules may be applied as biological material to the liquid channels in order to bind DNA strands which are contained in the analyte and have a DNA sequence that is complementary to the sequence of the DNA probe molecules.

The invention ensures that the reduced pressure produced in the capillary device is less than a critical pressure such that, if it is exerted in the capillary device, a surface tension which is produced by the first medium or a second medium, which is described below, in the capillary device, when the first medium has been taken up fully by the capillary device, would be overcome.

This prevents the second medium, which is present in a second phase which is different from the first phase, from being taken up into the capillary device after the first medium has been taken up fully.

Clearly, this means that in the capillary device, for example by means of a pump controller which controls a pump producing the reduced pressure in the capillary device in such a way that the reduced pressure, which is produced in the capillary device, is set in such a way that the reduced pressure does not exceed the surface tension of the first medium or, if e.g. the first medium is present in gas form and the second medium is present as a liquid, of the second medium in the capillary device.

The critical pressure in the capillary device is given, for example, by the following rule:

$$P = 2 \cdot \frac{S}{r},$$

where

BRIEF SUMMARY OF THE INVENTION

S denotes the surface tension which is produced by the first medium in the capillary device when the first medium has been taken up fully by the capillary device, r denotes the radius of a capillary device with a circular base.

In the event that the first medium is a liquid, the second medium may be a gas.

This configuration of the invention, as will be explained in more detail below, hence prevents any gas, for example air, from being taken up into the capillary device when all of the liquid from a container has been taken up by means of the capillary device, so that in this way the pump result, and concomitantly the analysis result when an analysis chip is used, is not compromised by the second medium.

However, the first medium may also be a gas, in which case the second medium is usually a liquid.

The invention clearly utilises the effect that a surface tension of the liquid, produced because of the capillary effect, automatically ensures that only the medium to be analysed is taken up into the capillary device since the second medium is not taken up, after the first medium has been taken up fully, owing to the surface tension of the latter. If the second medium is present as a liquid and the first medium is present as a gas, then after the first medium has been taken up fully into the capillary device, the surface tension of the second medium itself prevents its take-up.

This procedure is very simple, and the arrangement intended for carrying out the method can hence be produced very inexpensively.

The use of an analysis chip for analysing the medium taken up by the capillary device overall makes it possible, very simply and inexpensively, to have an arrangement for analysing a medium, for example an analyte for tissue analysis.

According to another configuration of the invention, the capillary device is a porous plate having a plurality of channels, the reduced pressure being in each case produced in one channel.

Each channel has, for example, a circular base with a radius of from 0.1 Fm to a few Fm, preferably up to approximately 10 Fm. If the cross section of the channel is not circular, the base is dimensioned in a size corresponding to the circular base.

Exemplary embodiments of the invention are represented in the figures and will be explained in more detail below.

FIG. 1 shows a sketch of an arrangement for taking up liquid analytes according to a first exemplary embodiment of the invention;

FIG. 2 shows a detail of the arrangement in FIG. 1 in cross section, in a state in which all of the analyte is located in the wells;

FIG. 3 shows the detail in FIG. 2, in the state such that some of the analytes have been sucked into a holding space by the pipettes;

FIG. 4 shows a cross section through a pipette, which is used to illustrate a principle on which the second exemplary embodiment of the invention is based.

FIG. 5 shows a cross section through a pipette, which is used to illustrate a principle on which the second exemplary embodiment of the invention is based.

FIG. 6 shows a cross section through a pipette, which is used to illustrate a principle on which the second exemplary embodiment of the invention is based.

FIRST EXEMPLARY EMBODIMENT

FIG. 1 shows an arrangement 100 for taking up liquid analytes according to a first exemplary embodiment of the invention.

This arrangement 100 has a microtitre plate 101 with a plurality of wells 102 for taking up analytes, i.e. liquids to be analysed, which are usually each different.

A further plate 103, which is coupled to the microtitre plate 101 by means of screws (not shown), is applied to the microtitre plate 101. The further plate 103 will be explained in more detail below.

Via the further plate 103 which, corresponding to the wells 102, respectively has pipettes as represented in FIG. 2, which pipettes are hermetically coupled to a pump 104 which is applied to the further plate 103.

By means of the pump 104, it is possible to set the pressure inside the further plate 103, as described below, i.e. an overpressure or a reduced pressure can be freely set in the corresponding space by the pump 104.

FIG. 2 shows an enlarged detail 105 of the arrangement 100 in FIG. 1.

As can be seen from FIG. 2, an analyte 201 to be analysed is usually introduced into each of the wells 102.

The pipettes 202 arranged in the further plate 103 are arranged in the further plate 103 in such a way that, when the further plate 103 is fastened on the microtitre plate 102 by means of the screws (not shown), a pipette 202 protrudes in each case into a well 102 assigned to it, and hence into the respective analyte 201.

The pipettes 202 are formed on a lower plastic body 203 of the further plate 103.

The lower plastic body 203 is coupled, for example adhesively bonded, to an upper plastic body 204.

According to this exemplary embodiment, an intermediate plate 205, in which of the analysis chips 206, according to this exemplary embodiment the analysis chip described in [2], which is also referred to as a Flow-Thru Chip™, is fitted in such a way that a respective analysis chip 206 is provided for each well, is arranged between the lower plastic body 203 and the upper plastic body 204.

Clearly, this means that one analysis chip 206 is in each case intended to analyse one analyte 201, which is respectively contained in a well 102 and, according to a method described below, is sucked via the pipette 202 and the lower plastic body 203 through the analysis chip 206, i.e. through the liquid channels of the analysis chip 206, into the upper plastic body 204.

In this way, the analyte 201 is in each case brought into intimate contact with the probe molecules on the surface of the liquid channels of the analysis chip 206.

On the upper plastic body 204, a respective diaphragm 207 is provided for each well 102.

This means that the upper plastic body 204 in each case forms a space, essentially corresponding to the upper surface shape of the well 102, which is respectively formed by side walls 208 of the upper plastic body 204.

Clearly, chambers 209 are hence formed in the upper plastic body 204, which are in each case bounded by the walls 208, the diaphragm 207 and the intermediate plate 205 with the integrated analysis chip 206.

The diaphragm 207 is in each case an elastic diaphragm, for example made of latex, which can be modified by means of a pressure change in a space 210 which is located over the upper plastic body 204 and is coupled to the pump 104.

The space 210 may be filled with gas or with a liquid, the diaphragm being impermeable to the corresponding gas, or the liquid with which the space 210 is filled.

Clearly, a pressure variation in the space 210 hence deforms the diaphragm 207 so that a pressure variation is produced in the respective chambers 209, by means of which the analyte 201, via the pipette 202, is either sucked through the analysis chip 206 or discharged into the well.

The liquid channels in the Flow-Thru Chip™ 206 are coated with biological material, i.e. with DNA probe molecules according to this exemplary embodiment, which are bound to the surface of the liquid channels in the analysis chip 206 by means of the known gold/sulphur coupling.

If the analyte 201 to be analysed has DNA strands with a sequence which is complementary to the DNA sequence of the DNA probe molecule, then these DNA strands bind covalently to the DNA probe molecules in the liquid channels of the analysis chip 206.

Clearly, the diaphragm 207 is hence deformed in each case by a pressure change, as represented in FIG. 3, according to the size of the diaphragm between the two extreme positions, symbolised in FIG. 3 by the tangents 211, 212 to the diaphragms which are in each case maximally curved.

Because of the deformation, as described above, the analyte is sucked in or released.

Furthermore, according to this exemplary embodiment, a buffer plate 213 which ensures improved mixing of the analyte 201 by the formation of a corresponding flow shape around the buffer plate 213, is provided in the lower plastic body 203 for each pipette 202, respectively between the pipette 202 and the intermediate plate 205.

According to this embodiment, it should be noted that the liquid amount of the analyte 201 pumped by means of the diaphragm 207 needs to be significantly greater than the volume, defined in each case for a pipette 202 by the lower plastic body 203, of a lower chamber 214 below the analysis chip 206.

After the analysis of the analyte has been carried out, which typically takes a few hours in the context of hybridisation, the arrangement 100 is emptied using a maximum diaphragm setting in the position 212.

BRIEF DESCRIPTION OF THE DRAWINGS

Rinsing procedures for the arrangement, using a rinsing solution, can be carried out in a similar way as for the analysing.

SECOND EXEMPLARY EMBODIMENT

The second exemplary embodiment corresponds essentially to the first exemplary embodiment, with the difference that no diaphragm 207 is needed.

In order to ensure that, after all of the analyte has been sucked up from a respective well, no air or another gas is sucked out of the well into the pipette, the pump 104 is operated in such a way that a surface tension, described below, which is formed in the analyte at the lower end of the respective pipette 202 is not exceeded.

Figure 4:
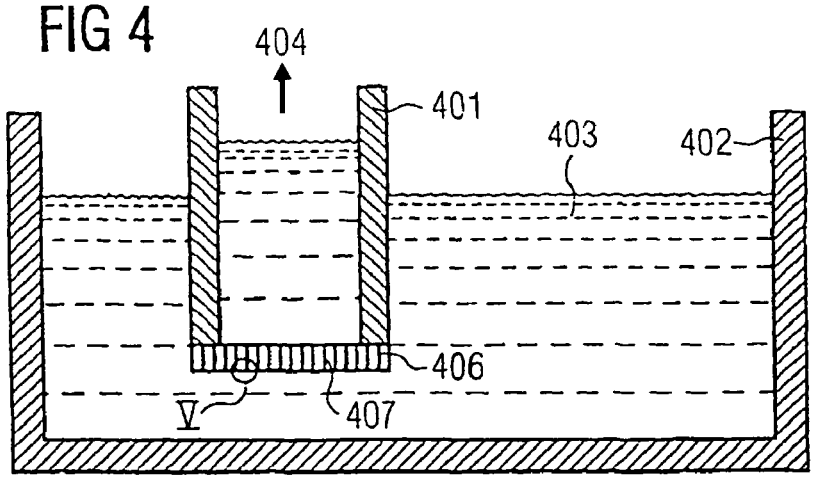

This principle is illustrated in FIG. 4.

FIG. 4 shows a pipette 401, which is dipped into a well 402 and thereby into the analyte 403.

A reduced pressure formed in the pipette 401 is symbolised in FIG. 4 by means of an arrow 404.

The pipette 401 according to this exemplary embodiment is configured as a tube with a diameter of approximately 1 cm and is sealed, for example adhesively bonded, at its lower end 405 to a diaphragm 406, the diaphragm 406 containing a plurality of pores 407, or at least one pore 407, with a preferably constant diameter, according to this exemplary embodiment a diameter of 10 Fm.

In general, such a pore 407 may, for example, have a diameter of from 0.1 Fm to 100 Fm.

A diaphragm 406 as disclosed by [3], made of glass or silicon, is used according to this exemplary embodiment.

It is assumed according to this exemplary embodiment, without restricting the generality, that the diaphragm 406 is hydrophilically configured.

The analyte 403 then penetrates the pores 407 of the diaphragm 406 and can be sucked into the pipette 401 by a small reduced pressure, for example 0.03 bar according to this exemplary embodiment.

Figure 5:
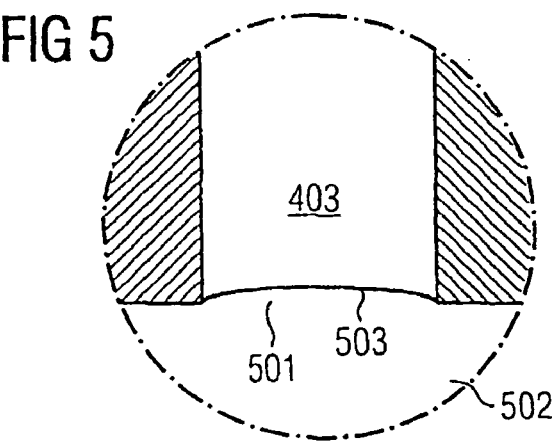

If the well 402 is emptied, i.e. the analyte 403 is taken up fully into the pipette 401, then a meniscus 503 is formed, as represented in FIG. 5, at each pore opening 501 between the analyte 403 and the air 502 which is all that remains in the well 402.

DETAILED DESCRIPTION OF THE INVENTION

In order to deform the meniscus 503 which is being formed, in such a way that it is possible for air 502 to enter the pore 407, it is necessary to produce a substantially stronger reduced pressure than the reduced pressure which is required in order to suck the analyte 403, in general a liquid, into the capillary, i.e. into the pipette 401.

This required pressure P can be estimated according to the following rule:

$$P = 2 \cdot \frac{S}{r},$$

where
- S denotes the surface tension of the respective liquid, i.e. of the analyte 403, and
- r denotes the radius of the respective pore 407.

These values are usually known for a given arrangement.

If water is used as the analyte and a pore 407 has a radius of 10 Fm, then a value of 0.29 bar is found for the required pressure P.

So that entry of air into the pore 407 can be prevented, it is necessary to ensure a pressure from the pump which is below this estimated pressure.

This control measure is usually noncritical since, as explained above, a reduced pressure of 0.03 bar is necessary in order to suck in the analyte, this pressure being an order of magnitude less than the critical pressure at which the surface tension would be overcome and air could enter the pore 407.

In other words, this means that the reduced pressure P produced in the pipette is in a range of 0.03<P<0.29 bar for this pipette with the dimensions stated above.

Entry of air into the pipette is hence prevented in a very simple way.

It is of course also possible, in the case of a hydrophobic diaphragm 406, similarly to pump a predefinable gas by means of the arrangement described above and to prevent entry of liquid through the respective pore, in general through a capillary.

Clearly, this exemplary embodiment makes it possible to ascertain automatedly whether all of the analyte 403 has been taken up from the respective well.

It is also automatedly ensured that no medium other than the material to be analysed is taken up into the analysis device.

Figure 6:
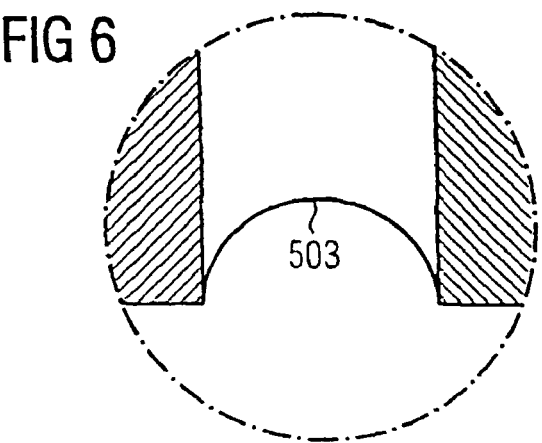

FIG. 6 shows the enlarged detail of a lower end of a pore 407 in FIG. 4 at a reduced pressure which lies in a range shortly before the air 502 enters the pore 407.

This is made clear by the strongly curved meniscus 503.

The following publications are cited in this document:

[1] M. Winter, Robotik und Automationskonzepte in der kombinatorischen Chemie—Synthese—und Pipettierroboter [Robotics and automation designs in combinatorial chemistry—synthesis and pipetting robots] Transkript Laborwelt, No 1, pp 25 ? 29, 2000;

[2] A. Steel et al., The Flow-Thru Chip: A Three-Dimensional Biochip Platform, Microarray Biochip Technology, edited by M. Schena, pp 87-117, 2000;

[3] EP 0 296 348 B1

LIST OF REFERENCE 100 arrangement
101 microtitre plate
102 well
103 further plate
104 pump
105 detail
201 analyte
202 pipette
203 lower plastic body
204 upper plastic body
205 intermediate plate
206 analysis chip
207 diaphragm
208 walls
209 upper chamber
210 space
211 first diaphragm position
212 second diaphragm position
213 buffer plate
214 lower chamber
401 pipette
402 well
403 analyte
404 arrow
405 lower region pipette
406 diaphragm
407 pore
501 pore opening
502 air
503 meniscus

The invention claimed is:

1. A method for taking up a medium to be analysed, the method comprising:
providing a pipette for taking up the medium to be analysed, the pipette having a diaphragm containing at least one pore of a given radius;
determining a critical pressure at which the surface tension of a liquid present at the at least one pore of said diaphragm would be overcome;
providing a pump that produces a negative pressure in the pipette to take up the medium to be analysed;
providing a pump controller that controls the pump so that the negative pressure does not go below the critical pressure; and
using the pump controller to control the pump to take up the medium to be analysed.

2. The method of claim 1, wherein determining a critical pressure comprises determining the critical pressure using:

$$P = 2 \cdot S/r$$

where S denotes the surface tension of the liquid present at the at least one pore, and r denotes the given radius of the at least one pore.

3. The method of claim 1, further comprising providing the medium to be analysed.

4. The method of claim 3, wherein providing the medium to be analysed comprises providing the liquid.

5. The method of claim 3, wherein providing the medium to be analysed comprises providing a gas.

6. The method of claim 1, wherein providing a pipette comprises providing a pipette having a diaphragm that is hydrophilic.

7. The method of claim 1, wherein providing a pipette comprises providing a pipette having a diaphragm that is hydrophobic.

8. A method for taking up a first medium to be analysed, the method comprising:
providing a pipette for taking up the first medium, the pipette having a diaphragm containing at least one pore of a given radius;
providing a pump that is capable of producing a negative pressure in the pipette;
providing a pump controller that controls the pressure produced by the pump;
providing the first medium and a second medium in a container, such that a boundary between the first medium and the second medium comprises a surface having a surface tension;
determining a critical pressure at which the surface tension would be overcome;
dipping the pipette into the first medium; and using the pump controller to control the negative pressure produced by the pump such that the negative pressure does not go below the critical pressure, so that the first medium is fully taken up and taking up of the second medium is prevented.

9. The method of claim 8, wherein determining a critical pressure comprises determining the critical pressure using:

$$P = 2 \cdot S/r$$

where S denotes the surface tension, and r denotes the given radius of the at least one pore.

10. The method of claim 8, wherein the first medium comprises a liquid and the second medium comprises a gas.

11. The method of claim 8, wherein the first medium comprises a gas and the second medium comprises a liquid.

12. The method of claim 8, wherein providing a pipette comprises providing a pipette having a diaphragm that is hydrophilic.

13. The method of claim 8, wherein providing a pipette comprises providing a pipette having a diaphragm that is hydrophobic.

* * * * *